United States Patent [19]
Lambert

[11] Patent Number: 5,609,165
[45] Date of Patent: Mar. 11, 1997

[54] FLEXIBLE THIMBLE TYPE FINGER PROTECTOR

[75] Inventor: Frank H. Lambert, Hertfordshire, United Kingdom

[73] Assignee: Stuart Wallace, Melford, United Kingdom

[21] Appl. No.: 204,190

[22] PCT Filed: Aug. 13, 1992

[86] PCT No.: PCT/GB92/01498

§ 371 Date: May 3, 1994

§ 102(e) Date: May 3, 1994

[87] PCT Pub. No.: WO93/04638

PCT Pub. Date: Mar. 18, 1993

[30] Foreign Application Priority Data

Sep. 4, 1991 [GB] United Kingdom .................. 9118928
Jan. 31, 1992 [GB] United Kingdom .................. 9202095

[51] Int. Cl.⁶ ............................. A61F 5/37; A41D 19/00; D05B 91/04
[52] U.S. Cl. ............................. 128/879; 2/163; 2/161.7; 223/101; 138/89
[58] Field of Search .................. 2/21, 163, 161.7, 2/161.6, 159; 223/101; 128/879, 880, 888, 846; 138/89, 94

[56] References Cited

U.S. PATENT DOCUMENTS

| 113,601 | 4/1871 | Wansleben | 223/101 |
|---|---|---|---|
| 467,258 | 1/1892 | Nicolai | 138/89 |
| 859,771 | 7/1907 | Holden | 223/103 |
| 2,039,505 | 5/1936 | Vollmer . | |
| 2,143,927 | 1/1939 | Thompson | 128/880 |
| 3,290,695 | 12/1966 | Burtoff | 2/161 |
| 3,511,242 | 5/1970 | Agnone . | |
| 4,507,804 | 4/1985 | Consigny | 2/21 |
| 4,825,470 | 5/1989 | Horio | 2/21 |
| 4,873,998 | 11/1989 | Joyner | 128/879 |

FOREIGN PATENT DOCUMENTS

| 137988 | 4/1985 | Germany . | |
| 3637620 | 5/1988 | Germany . | |
| 667295 | 2/1952 | United Kingdom . | |
| 2267023 | 11/1993 | United Kingdom | 2/21 |

*Primary Examiner*—Robert A. Hafer
*Assistant Examiner*—Michael O'Neill
*Attorney, Agent, or Firm*—Woodcock Washburn Kurtz Mackiewicz & Norris

[57] ABSTRACT

The invention includes a finger protector comprising a tube-like portion with a closed end, the wall of the tube being formed of at least one elongate strip of a material which strongly resists penetration by a needle and which is in helical configuration. The strip is of such cross section that adjacent edges of adjacent turns of the helix or helices interlock to prevent the turns separating axially but allowing a limited amount of axial movement such that, when worn on a finger, the finger may be bent to a limited extent without adjacent turns separating.

8 Claims, 3 Drawing Sheets

FLEXIBLE THIMBLE TYPE FINGER PROTECTOR

My invention relates to a finger protector particularly for use by doctors, dentists, surgeons and veterinary workers to protect their fingers from penetration by needles or bone and tooth splinters when working on portions of the body, e.g. when retracting bone and muscle portions during entry to the chest cavity, or when performing alveolar grafts or closing up after surgical or dental operations. They may also find application in the industrial field, e.g. when using industrial sewing machines, and the like.

During surgical operations it is frequently necessary for sewing to be performed under difficult conditions where access is restricted since the sewing site is within a body cavity accessed through a surgical incision. Under such circumstances the fingers of one hand may be required to hold parts together whilst the other hand manipulates the needle to perform the sewing together of those parts. With such restricted access it is very easy for the fingers of the one hand to be pricked by the needle which may cause infection of either the surgeon, or the patient, with Hepatitis or H.I.V., if one of them should be a carrier of the disease.

In order to prevent such injuries it has been suggested that the surgeon should use two or more pairs of gloves however such measures are not particularly effective since it is still possible for the needle to penetrate to the fingers, and it restricts movement and blood circulation in the fingers.

Alternatively a glove from material comprising, at least in part, metal wire has been suggested, to wear under the normal surgical glove. However such an inner glove, while providing excellent protection against cuts, does not provide complete protection against needle stab wounds, since the needle can penetrate the interstices of the woven material.

In order to provide complete protection of the fingers, while still permitting a reasonable amount of flexibility of the fingers and sensitivity to the touch of a needle or scalpel, my invention provides a finger protector comprising a tube-like portion with a closed end, shaped and sized to fit over the finger of a wearer characterised in that the wall of said tube-like portion is formed of at least one substantially circumferentially extending strip member of a material which strongly resists penetration by a needle, said strip member being so formed that adjacent edges of said strip member interlock to prevent the said strip member separating axially but allow a limited amount of axial movement such that, when worn on a finger, the finger may be bent to a limited extent without adjacent said strip member portions separating.

The adjacent strip like portions may be formed by adjacent rings or by adjacent turns of one or more helically wound strips, and the interlocking engagement of the strip like portions maybe provided by the adjacent strip portions having radially oppositely directed, channel sections with the outer side wall of each channel section engaging in the channel section of the adjacent strip portion to form a continuous sleeve which permits axial extension or contraction movement without allowing axial separation.

In one embodiment the tubular portion is formed by alternate inward and outward facing channel section rings, with the radial walls of each ring engaging in the channels of respective adjacent rings, while in another embodiment the tubular portion is formed of two helical members of radially oppositely directed channel section with the two members arranged such that the side walls of one channel member locate respectively in the channel of two adjacent turns of the other member.

Specific embodiments of the invention will now be described, by way of example, with reference to the accompanying drawings of which:

Figure 3:
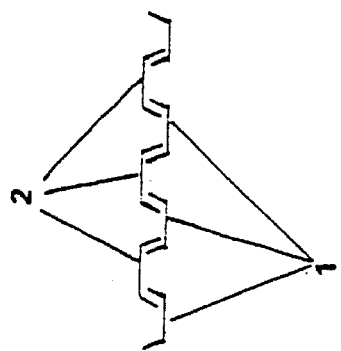
FIG. 3 Shows the cross section of the strip used in the embodiment of FIG. 1.
Figure 1:
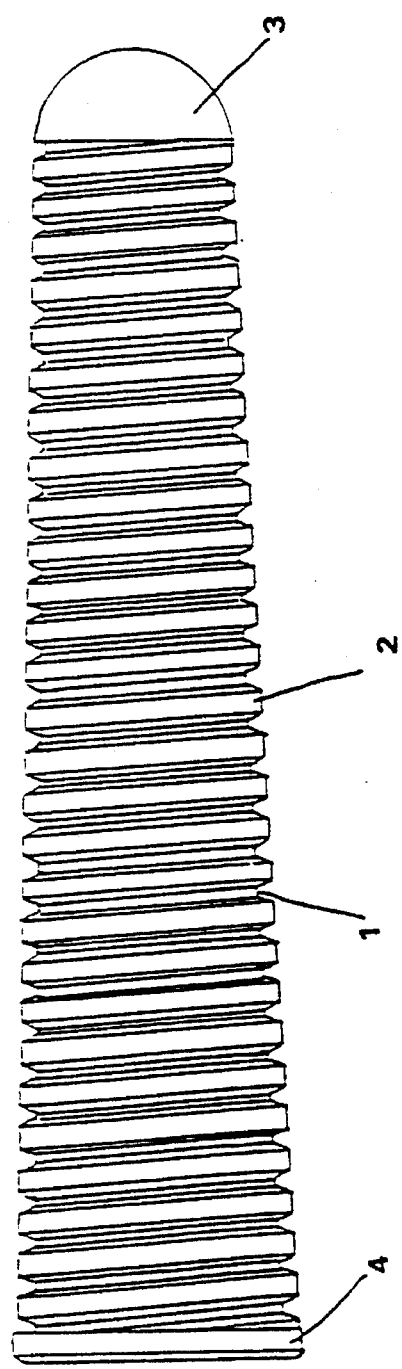
FIG. 1 Shows an elevation of one embodiment of the invention.
Figure 2:
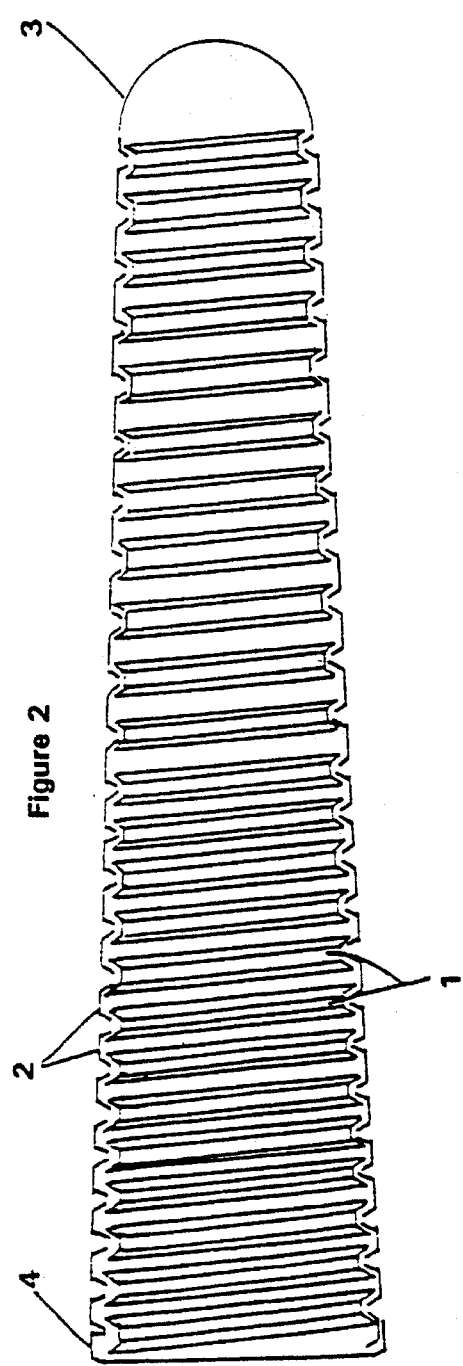
FIG. 2 Shows a longitudinal section of the embodiment of FIG. 1.

FIG. 1 Shows a first embodiment of the complete finger protector which as can be seen from FIGS. 2 & 3 is formed of two elongate strips 1, 2, of channel section a first of which (1) is helically wound on a mandrel, with the open channel facing outwardly from the mandrel. The second channel strip (2) is wound over the first channel strip, with the open channel section facing inwardly toward the mandrel and with the walls of the channel engaging one in each of the open channels of adjacent turns of the first channel strip (1). We have found that the two strips can be wound simultaneously using a spring forming machine. If the strip members are of metal they will normally be self maintaining in their helical form but plastics extruded strips may require heat treatment to ensure that they maintain their helical configuration, or they may be wound on the mandrel direct from the extruder, or after preheating, so that they cool and set in the desired helical configuration.

Figure 11:
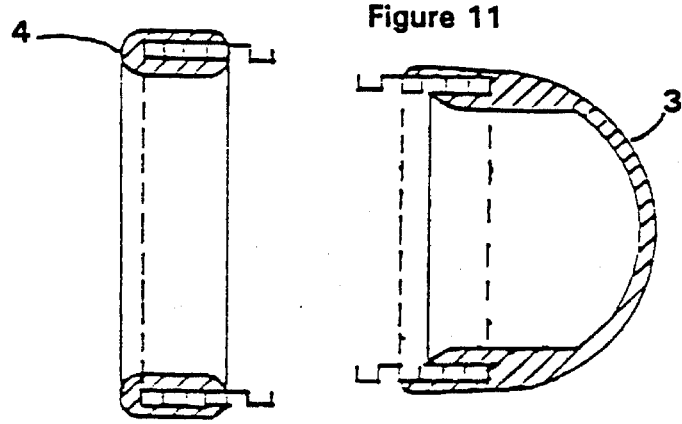
FIG. 11 Shows a possible form of end cap and edge guard for the protector.

An end cap (3) is secured to the smaller diameter end of the members, e.g. by soldering, welding, heat, acoustic or adhesive bonding and the open end may be secured in a ring (4), again by soldering, welding, heat, acoustic or adhesive bonding, or by frictional engagement between two rings. The ring (4) may be contoured to the base of the finger. The cap (3) and ring (4) are preferably plastics mouldings, as shown in FIG. 11 and may be colour coded and/or marked to indentify the protector size and/or purpose. The protection member can be formed with a mainly round cross section with a flattened tip to aid in gripping articles, however the whole member could be formed with a non circular cross section, e.g. having portions of the circumference of differing radius of curvature which may increase the flexibility in the direction of finger movement. An advantage of the circular cross section is that slight torsional movement of one end of the member relative to the other adjusts the internal diameter of the member, assisting insertion or removal of the finger.

Figure 4:
FIGS. 4 to 8 Show alternative cross sections of the strips used to form the protector of FIG. 1.
Figure 5:
Figure 6:
Figure 7:
Figure 8:
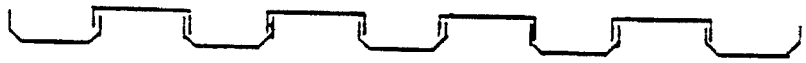

The preferred embodiment uses two strips of channel section, such as shown in FIG. 3, however alternative sections may be used such as shown in FIGS. 4, 5, or 8. Alternatively a single strip of double channel section such as shown in FIGS. 6 or 7 might be used, with however a slight reduction in flexibility.

The strip members can be of metal such as stainless steel rolled into the required cross section, or of suitable plastics material extruded in the required cross section, and then helically wound onto a mandrel of suitable size as described above, however it would be possible to form the entire member by injection moulding.

Figure 9:
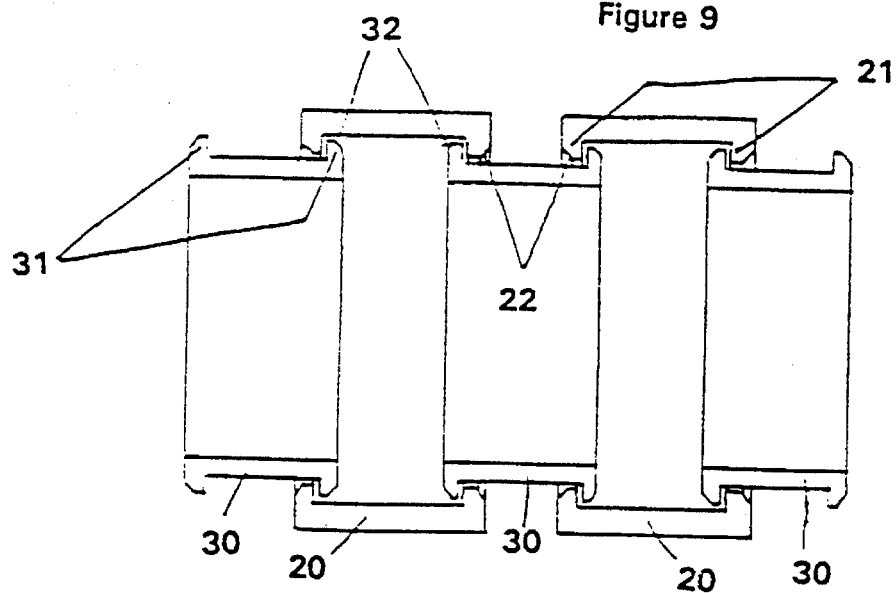
FIG. 9 Shows an alternative form of construction for the tubular portion of the protector of FIG. 1.

A second embodiment of the finger protector of my invention comprises an assembly as shown in FIG. 9 in which the tubular portion is formed of rings 30 with outwardly open channels alternating with rings 20 with inwardly open channels, with the walls of the channel of each ring locating in the channel of the respective adjacent ring.

Figure 10:
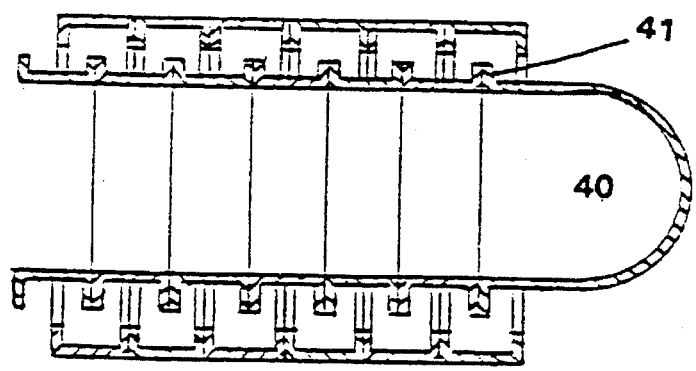
FIG. 10 Illustrates a possible method of manufacture of the alternative construction of FIG. 9.

The rings may be of such diameter that the flanges 21 and 31 are an interference fit, one with the other, and the rings assembled to form the tubular member 1, by forcing the flanges of one ring past the flanges of the other ring, chamfers 22,32 assisting the engagement. Alternatively the diameters may be such as to provide a clearance fit and the tube formed by inserting a stacks of rings of one form inside a stack of rings of the other form with the stacks slightly displaced so that the flanges of one stack align with the channels of the other stack, as shown in FIG. 10, and then applying radial force to either compress the diameter of the outer stack of rings, or expand the diameter of the inner stack of rings, so the flanges, of each stack enter the channels of the other stack to prevent complete axial separation of the rings while allowing some axial movement, or bending, of the tube so formed. Some rings may be of extended length where flexibility is not required, e.g. between knuckle joints, while the end closure may also be extended. The rings may also be non-circular form either as originally produced or after being formed during expansion of the inner set of rings, or compression of the outer set of rings, to effect the interlocking of adjacent rings. In addition the outer surface of the finger protector may be roughened to make a non-slip surface.

The rings and end cap may be of metal, such as stainless steel, or, preferably, moulded in a plastics material with heat applied during the deforming step to heat set the rings in the interlocked configuration.

End Caps may be provided as described above with respect to FIG. 11 or the closed end of the tube can be formed by a member 40 shaped to encompass the finger tip and having a flange 41 at its openend, either inwardly or outwardly extending, to engage in the channel of the adjacent, end, ring of the tubesection.

Figure 12:
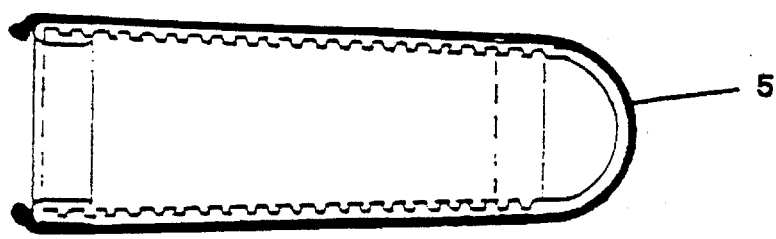
FIG. 12 Shows a modification of the protector of the invention.

As shown in FIG. 12 the finger protector may be provided with an outer sheath 5 of resilient flexible material such as is used for surgical gloves, to resiliently enclose and form a seal over the entire outer surface of the protector to prevent blood or other debris entering the channels thereof. The sheath may be separate from the protector and held in place by its own resilience where it overlaps the ring at the open end of the protector or it may be bonded to or integral with the ring 4. The outer cover could be bonded to the end cap and/or the outer surface of the protector tubular portion, but bonding to the tubular portion could adversely affect the flexibility.

The protection members would be formed in a range of sizes, to fit different size fingers, or of different shape to fit different fingers, or thumbs, and could be worn inside or outside a conventional surgical glove, and may be sterilied for re-use or may, preferably, be disposable.

In the drawings the relative dimensions of the protector components have been distorted in the interests of clarity. In an actual production protector the diameter of the assembly could be about 2 to 2.5 cms. the strips or rings would be of material about 0.127 mm thick with the walls of the channel section extending about 0.4 mm above the floor of the channel section and there being about 0.1 mm clearance between the top of the wall and the bottom of the channel in which the wall locates. The dimensions would of course be varied dependant on the material of which the protector was contructed and the flexibility required in the assembly.

Whilst preferred embodiments of my invention have been described various alternative forms, and methods of manufacture, would be obvious to those skilled in the art and therefore the description of the preferred embodiments should not be considered as limiting the scope of the invention, which is defined by the following claims.

I claim:

1. A finger protector comprising a tube-like portion with a closed end, the wall of said tube being formed of at least two elongate strips of a material which strongly resists penetration by a needle and which are in helical configuration, said strips being of such cross section that adjacent edges of adjacent turns of the helices interlock to prevent the turns separating axially but allowing a limited amount of axial movement such that said tube-like portion may be bent to a limited extent without adjacent turns separating, wherein said cross section is selected from the group consisting of U-shaped, S-shaped or in a shape consisting of two U-shapes fused at one edge.

2. The finger protector of claim 1, wherein said tube-like portion is formed of two elongate channel section strips in helical configuration one strip being an inner strip positioned so that the channel opens radially outwardly and the other strip being an outer strip positioned so that the channel opens radially inwardly with the walls of the channel of the outer strip each positioned in a respective channel of two adjacent turns of the inner strip.

3. The finger protector of claim 1 or 2, comprising a transverse cross section over at least the tip portion of its length which is asymmetric with a larger radius of curvature over a portion of its circumference than the radius of curvature of the remainder of its circumference, thereby forming a flattened tip.

4. The finger protector of claim 1, formed by winding said at least one elongate strip helically on a shaped mandrel to form a shaped tube and attaching a cap on one end.

5. The finger protector of claim 4, wherein said elongate strip is formed of extruded plastics, which strip is wound on a mandrel and heat treated either before or after winding to form the helical configuration upon cooling.

6. The finger protector of claim 1, wherein said at least one elongate strip is of metal, rolled on the appropriate cross section.

7. The finger protector of claim 1 formed of plastics material.

8. The finger protector of claim 7 formed by injection molding.

* * * * *